US011266092B2

(12) United States Patent
Chen et al.

(10) Patent No.: US 11,266,092 B2
(45) Date of Patent: Mar. 8, 2022

(54) AGRICULTURAL PRODUCT FOR IMPROVING IMMUNITY

(71) Applicant: SICHUAN HUI TAI AGRICULTURAL TECHNOLOGY CO. LTD., Chengdu (CN)

(72) Inventors: Lezhang Chen, Chengdu (CN); Junbo Yang, Chengdu (CN)

(73) Assignee: SICHUAN HUI TAI AGRICULTURAL TECHNOLOGY CO. LTD., Sichuan (CN)

(*) Notice: Subject to any disclaimer, the term of this patent is extended or adjusted under 35 U.S.C. 154(b) by 52 days.

(21) Appl. No.: 16/734,513

(22) Filed: Jan. 6, 2020

(65) Prior Publication Data
US 2020/0221663 A1 Jul. 16, 2020

(30) Foreign Application Priority Data

Jan. 14, 2019 (CN) .......................... 201910030325.7

(51) Int. Cl.
A01H 6/46 (2018.01)
A01N 63/32 (2020.01)
A01C 1/06 (2006.01)
A01H 5/10 (2018.01)
A01N 59/16 (2006.01)
A01C 1/00 (2006.01)
A01C 21/00 (2006.01)
C05F 11/00 (2006.01)
C05D 9/02 (2006.01)
C05G 5/20 (2020.01)
A23L 33/00 (2016.01)
A01H 3/04 (2006.01)
A23L 7/10 (2016.01)
C05G 3/00 (2020.01)
A01G 22/22 (2018.01)

(52) U.S. Cl.
CPC ............. *A01H 6/4636* (2018.05); *A01C 1/00* (2013.01); *A01C 1/06* (2013.01); *A01C 21/00* (2013.01); *A01G 22/22* (2018.02); *A01H 3/04* (2013.01); *A01H 5/10* (2013.01); *A01N 59/16* (2013.01); *A01N 63/32* (2020.01); *A23L 7/10* (2016.08); *A23L 33/00* (2016.08); *C05D 9/02* (2013.01); *C05F 11/00* (2013.01); *C05G 3/00* (2013.01); *C05G 5/20* (2020.02); *A23V 2002/00* (2013.01)

(58) Field of Classification Search
CPC .......... A01H 6/4636; A01H 5/10; A01H 3/04; A01N 63/32; A01N 59/16; A01C 1/06; A01C 21/00; A01C 1/00; A01G 22/22; A23L 7/10; A23L 33/00; C05D 9/02; C05F 11/00; C05G 3/00; C05G 5/20; A23V 2002/00
See application file for complete search history.

*Primary Examiner* — Sue X Liu
*Assistant Examiner* — Andriae M Holt
(74) *Attorney, Agent, or Firm* — SZDC Law P.C.

(57) ABSTRACT

A method of producing an agricultural product for improving immunity, the agriculture product being rice, includes: (1) soaking seeds of the agricultural product in a solution containing a magnetic material and a β-glucan; (2) before planting the seeds, applying a bottom fertilizer to a paddy field for the agricultural product, the bottom fertilizer including an organic fertilizer, the magnetic material, an oyster shell powder, the β-glucan and an organic zinc; and (3) at tillering stage, applying a topdressing to the paddy filed, the topdressing including the β-glucan and the organic zinc.

10 Claims, No Drawings

AGRICULTURAL PRODUCT FOR IMPROVING IMMUNITY

The present invention claims priority to Chinese Patent Application No. 201910030325.7, filed on Jan. 14, 2019, which is incorporated by reference for all purposes as if fully set forth herein.

FIELD OF THE INVENTION

The present invention relates to an agricultural product for improving immunity and a method for preparing the same.

BACKGROUND OF THE INVENTION

With the improvement of living standards, people's requirements for agricultural products have become higher and higher. For example, agricultural products need have better nutritional and health functions and can improve human immunity.

In order to meet these requirements, it is reported that selenium-rich rice can improve human immunity. Excessive amounts of selenium, however, can cause poisoning.

β-Glucan is a polysaccharide consisting of glucose, widely present in microorganisms and plants. The main chemical structures of β-glucan include β-1,3 glucan and β-1,6 glucan. The former has antitumor properties and can improve immunity. Experiments have shown that β-glucan, especially β-1,3 glucan, can promote the production of IgM antibodies to improve the humoral immunity. In addition, β-glucan can remove free radicals, resist radiation, dissolve cholesterol, prevent hyperlipidemia and resist infections caused by viruses, fungi, bacteria, and the like.

In regular rice, the β-glucan content is low, generally about 0.8-1.0 wt %. At present, many methods for increasing the content of β-glucan in crops have been reported, but these methods generally have the disadvantages of high cost, unsuitable for large-scale cultivation, and the low increase of β-glucan content.

In addition, zinc, as one of the essential elements, is a component of more than 100 kinds of enzymes in the human body, and plays an important role in the development of the immune system and the maintenance of normal immune functions. Therefore, an appropriate amount of zinc supplementation can also improve human immunity. At present, the content of zinc in ordinary rice is very low, generally less than 2 mg/kg, and to increase the content of zinc in rice is a technical problem that has been tried to solve in the art.

SUMMARY OF THE INVENTION

In one embodiment, a method of producing an agricultural product for improving immunity, the agriculture product being rice, includes: (1) soaking seeds of the agricultural product in a solution containing a magnetic material and a β-glucan; (2) before planting the seeds, applying a bottom fertilizer to a paddy field for the agricultural product, the bottom fertilizer including an organic fertilizer, the magnetic material, an oyster shell powder, the β-glucan and an organic zinc; and (3) at tillering stage, applying a topdressing to the paddy filed, the topdressing including the β-glucan and the organic zinc.

In another embodiment, the method further includes at grain filling stage, spraying the β-glucan and the organic zinc to the agricultural product.

In another embodiment, the magnetic material is a mixture of a ferrite powder and a magnetite powder.

In another embodiment, the β-glucan is a yeast β-glucan.

In another embodiment, the organic zinc is zinc gluconate or zinc ferment.

In another embodiment, the solution is an aqueous solution containing 2-5 wt % of the magnetic material by weight and 1-1.5 wt % of the β-glucan, based on the weight of the aqueous solution.

In another embodiment, the seeds are sonicated in the solution for 30-60 minutes.

In another embodiment, the bottom fertilizer includes 5-8 wt % of the magnetic material, 15-25 wt % of the oyster shell powder, 3-5 wt % of the β-glucan and the 2-5 wt % of the organic zinc, based on the weight of the organic fertilizer.

In another embodiment, the organic fertilizer, the magnetic material, the oyster shell powder, the β-glucan and the organic zinc are stirred for at least 20 minutes at 45-60° C. before applying the bottom fertilizer.

In another embodiment, the topdressing includes 3-5 wt % of the β-glucan and 2-5 wt % the organic zinc, based on the weight of the topdressing.

In another embodiment, the β-glucan and the organic zinc are dissolved in 200-500 times weight of water before spraying to the agricultural product.

Compared with conventional technology, the present invention has the advantages that the content of β-glucan in rice can reach 6.76 wt %. 90% of the β-glucan is β-1,3 glucan. Iron content can reach 25.7 mg/kg and zinc content can reach 16.8 mg/kg, which are significantly higher than regular rice. The increase in iron content can help the body to absorb β-glucan. Rice with high β-glucan and zinc contents can enhance human immunity.

It is to be understood that both the foregoing general description and the following detailed description are exemplary and explanatory and are intended to provide further explanation of the invention as claimed.

DETAILED DESCRIPTION OF THE ILLUSTRATED EMBODIMENTS

Reference will now be made in detail to embodiments of the present invention.

The magnetic material of the present invention refers to a material capable of responding to a magnetic field in a certain way, especially a ferromagnetic material. The magnetic material is used to stimulate the potential of crops and improve crop nutrition molecules production, such as inducing β-glucan production in plants. The magnetic material is used with zinc synergistically to improve the cultivation of β-glucan.

The oyster shell powder of the present invention is the powder of oyster shell. The oyster shell powder contains a large amount of calcium carbonate and essential trace elements, i.e., copper, magnesium, potassium, molybdenum, phosphorus, manganese, iron, zinc, etc. In addition, the oyster shell powder also contains a variety of amino acid components.

In the present application, the magnetic materials, β-glucan, and organic zinc are used together synergistically to significantly increase the content of β-glucan, zinc, iron and other elements in crops.

The β-glucan of present application can be yeast β-glucan (a polysaccharide existing in the yeast cell wall, also known as dextran) or barley β-glucan (the main component of the endosperm cell wall of barley seed, the chemical name: (1-3)

(1-4)-β-D-glucan). The use of β-glucan with fertilizer is more conducive to the formation and proliferation of β-glucan in rice.

EXAMPLE 1

An agricultural product for improving immunity, the agriculture product being rice. The rice is grown by a conventional growing method and the following additional steps:

(1) adding a magnetic material and β-glucan to an aqueous solution and soaking the rice seeds in the aqueous solution.

The magnetic material was a mixture of a ferrite powder (commercially available) and a magnetite powder (commercially available). The weight ratio of the ferrite powder and the magnetite powder is 1:3. The aqueous solution includes 3 wt % of the magnetic material.

The β-glucan is yeast β-glucan (commercially available), and the aqueous solution includes 1.5 wt % of the yeast β-glucan.

After adding the magnetic material and β-glucan, the aqueous solution is for 50 minutes, and the seeds are then soaked in the solution.

(2) before planting the seeds, applying a bottom fertilizer to a paddy field for rice, the bottom fertilizer including an organic fertilizer, the magnetic material, an oyster shell powder, the β-glucan and an organic zinc.

The organic fertilizer is a commercially available organic fertilizer or farm organic fertilizer.

The oyster shell powder is commercially available, and the bottom fertilizer includes 21 wt % of the oyster shell powder, based on the weight of the bottom fertilizer.

The β-glucan is a 1:1 mixture of yeast β-glucan and barley β-glucan.

The organic zinc is a 1:1 mixture of zinc gluconate and zinc ferment.

The organic fertilizer, the magnetic material, the oyster shell powder, the β-glucan and the organic zinc are stirred for 30 minutes at 55° C. before applying the bottom fertilizer.

(3) at tillering stage, applying a topdressing to the paddy filed, the topdressing including the β-glucan and the organic zinc.

The β-glucan is yeast β-glucan (commercially available), and the topdressing includes 5 wt % of the yeast β-glucan.

The organic zinc is zinc ferment, and the topdressing includes 5% of the zinc ferment.

The yeast β-glucan and zinc ferment are mixed well before applying to the paddy field.

(4) at grain filling stage, spraying the β-glucan and organic zinc to rice.

The β-glucan is yeast β-glucan (commercially available), and the organic zinc is zinc gluconate (commercially available).

The yeast β-glucan and zinc gluconate are added to the 300 times weight of water and completely dissolved in water. The solution is then sprayed to the rice.

The rice grown by this method is "Rice A."

EXAMPLE 1

An agricultural product for improving immunity, the agriculture product being rice. The rice is grown by a conventional growing method and the following additional steps:

(1) adding a magnetic material and β-glucan to an aqueous solution and soaking the rice seeds in the aqueous solution.

The magnetic material was a mixture of a ferrite powder (commercially available) and a magnetite powder (commercially available). The weight ratio of the ferrite powder and the magnetite powder is 1:3. The aqueous solution includes 3 wt % of the magnetic material.

The β-glucan is yeast β-glucan (commercially available), and the aqueous solution includes 1.5 wt % of the yeast β-glucan.

After adding the magnetic material and β-glucan, the aqueous solution is for 50 minutes, and the seeds are then soaked in the solution.

(2) before planting the seeds, applying a bottom fertilizer to a paddy field for rice, the bottom fertilizer including an organic fertilizer, the magnetic material, an oyster shell powder, the β-glucan and an organic zinc.

The organic fertilizer is a commercially available organic fertilizer or farm organic fertilizer.

The magnetic material was a mixture of the ferrite powder (commercially available) and the magnetite powder (commercially available). The weight ratio of the ferrite powder and the magnetite powder is 1:2. The bottom fertilizer includes 6 wt % of the magnetic material, based on the weight of the bottom fertilizer.

The oyster shell powder is commercially available, and the bottom fertilizer includes 21 wt % of the oyster shell powder, based on the weight of the bottom fertilizer.

The β-glucan is a 1:1 mixture of yeast β-glucan and barley β-glucan.

The organic zinc is a 1:1 mixture of zinc gluconate and zinc ferment.

The organic fertilizer, the magnetic material, the oyster shell powder, the β-glucan and the organic zinc are stirred for 30 minutes at 55° C. before applying the bottom fertilizer.

(3) at tillering stage, applying a topdressing to the paddy filed, the topdressing including the β-glucan and the organic zinc.

The β-glucan is yeast β-glucan (commercially available), and the topdressing includes 5 wt % of the yeast β-glucan.

The organic zinc is zinc ferment, and the topdressing includes 5 wt % of the zinc ferment.

The yeast β-glucan and zinc ferment are mixed well before applying to the paddy field.

(4) at grain filling stage, spraying the β-glucan and organic zinc to rice.

The β-glucan is yeast β-glucan (commercially available), and the organic zinc is zinc gluconate (commercially available).

The yeast β-glucan and zinc gluconate are added to the 300 times weight of water and completely dissolved in water. The solution is then sprayed to the rice.

The rice grown by this method is "Rice A."

EXAMPLE 2

An agricultural product for improving immunity, the agriculture product being rice. The rice is grown by a conventional growing method and the following additional steps:

(1) adding a magnetic material and β-glucan to an aqueous solution and soaking the rice seeds in the aqueous solution.

The magnetic material was a mixture of a ferrite powder (commercially available) and a magnetite powder (commercially available). The weight ratio of the ferrite powder and the magnetite powder is 1:3.5. The aqueous solution includes 5 wt % of the magnetic material.

The β-glucan is yeast β-glucan (commercially available), and the aqueous solution includes 1.3 wt % of the yeast β-glucan.

After adding the magnetic material and β-glucan, the aqueous solution is for 50 minutes, and the seeds are then soaked in the solution.

(2) before planting the seeds, applying a bottom fertilizer to a paddy field for rice, the bottom fertilizer including an organic fertilizer, the magnetic material, an oyster shell powder, the β-glucan and an organic zinc.

The organic fertilizer is a commercially available organic fertilizer or farm organic fertilizer.

The magnetic material was a mixture of the ferrite powder (commercially available) and the magnetite powder (commercially available). The weight ratio of the ferrite powder and the magnetite powder is 1:5. The bottom fertilizer includes 5 wt % of the magnetic material, based on the weight of the bottom fertilizer.

The oyster shell powder is commercially available, and the bottom fertilizer includes 15 wt % of the oyster shell powder, based on the weight of the bottom fertilizer.

The β-glucan is yeast β-glucan.

The organic zinc is a 1:1 mixture of zinc gluconate and zinc ferment.

The organic fertilizer, the magnetic material, the oyster shell powder, the β-glucan and the organic zinc are stirred for 40 minutes at 45° C. before applying the bottom fertilizer.

(3) at tillering stage, applying a topdressing to the paddy filed, the topdressing including the β-glucan and the organic zinc.

The β-glucan is yeast β-glucan (commercially available), and the topdressing includes 3 wt % of the yeast β-glucan.

The organic zinc is zinc ferment, and the topdressing includes 2 wt % of the zinc ferment.

The yeast β-glucan and zinc ferment are mixed well before applying to the paddy field.

(4) at grain filling stage, spraying the β-glucan and organic zinc to rice.

The β-glucan is yeast β-glucan (commercially available), and the organic zinc is zinc gluconate (commercially available).

The yeast β-glucan and zinc gluconate are added to the 500 times weight of water and completely dissolved in water. The solution is then sprayed to the rice.

The rice grown by this method is "Rice B."

EXAMPLE 3

An agricultural product for improving immunity, the agriculture product being rice. The rice is grown by a conventional growing method and the following additional steps:

(1) adding a magnetic material and β-glucan to an aqueous solution and soaking the rice seeds in the aqueous solution.

The magnetic material was a mixture of a ferrite powder (commercially available) and a magnetite powder (commercially available). The weight ratio of the ferrite powder and the magnetite powder is 1:2. The aqueous solution includes 3 wt % of the magnetic material.

The β-glucan is yeast β-glucan (commercially available), and the aqueous solution includes 1.5 wt % of the yeast β-glucan.

After adding the magnetic material and β-glucan, the aqueous solution is for 50 minutes, and the seeds are then soaked in the solution.

(2) before planting the seeds, applying a bottom fertilizer to a paddy field for rice, the bottom fertilizer including an organic fertilizer, the magnetic material, an oyster shell powder, the β-glucan and an organic zinc.

The organic fertilizer is a commercially available organic fertilizer or farm organic fertilizer.

The magnetic material was a mixture of the ferrite powder (commercially available) and the magnetite powder (commercially available). The weight ratio of the ferrite powder and the magnetite powder is 1:2. The bottom fertilizer includes 6 wt % of the magnetic material, based on the weight of the bottom fertilizer.

The oyster shell powder is commercially available, and the bottom fertilizer includes 21 wt % of the oyster shell powder, based on the weight of the bottom fertilizer.

The β-glucan is yeast β-glucan.

The organic zinc is a 1:1 mixture of zinc gluconate and zinc ferment.

The organic fertilizer, the magnetic material, the oyster shell powder, the β-glucan and the organic zinc are stirred for 30 minutes at 60° C. before applying the bottom fertilizer.

(3) at tillering stage, applying a topdressing to the paddy filed, the topdressing including the β-glucan and the organic zinc.

The β-glucan is yeast β-glucan (commercially available), and the topdressing includes 3.5 wt % of the yeast β-glucan.

The organic zinc is zinc gluconate (commercially available), and the topdressing includes 3 wt % of the zinc ferment.

The yeast β-glucan and zinc ferment are mixed well before applying to the paddy field.

(4) at grain filling stage, spraying the β-glucan and organic zinc to rice.

The β-glucan is yeast β-glucan (commercially available), and the organic zinc is zinc gluconate (commercially available).

The yeast β-glucan and zinc gluconate are added to the 200 times weight of water and completely dissolved in water. The solution is then sprayed to the rice.

The rice grown by this method is "Rice C."

COMPARATIVE EXAMPLE 1

This example is conducted in the same way as Example 1 except that steps (1) and (2) do not include adding the magnetic material. The rice grown by this method is "Control A."

COMPARATIVE EXAMPLE 2

This example is conducted in the same way as Example 1 except that step (1) does not include adding the magnetic material and step (2) does not include adding the magnetic material and oyster shell powder. The rice grown by this method is "Control B."

COMPARATIVE EXAMPLE 3

This example is conducted in the same way as Example 1 except that step (2) does not include adding the oyster shell powder. The rice grown by this method is "Control C."

COMPARATIVE EXAMPLE 4

This example is conducted in the same way as Example 1 except that steps (1), (2), (3), and (4) do not include adding the organic zinc. The rice grown by this method is "Control D."

Blank Control Example

This example is conducted in accordance with conventional method and steps (1), (2), (3), and (4) are not conducted. The rice grown by this method is "Blank Control."

The content of β-glucan, iron and zinc in the above products were measured in accordance with the methods of NY/T 2006-2011, GB/T 5009.90-2003 and GB/T 5009.14-2003. The results are shown in Table 1.

TABLE 1

β-glucan, Iron, and Zinc Contents

|  | β-glucan (%) | Iron (mg/kg) | Zinc (mg/kg) |
| --- | --- | --- | --- |
| Rice A | 6.76 | 25.7 | 16.8 |
| Rice B | 6.31 | 23.9 | 15.8 |
| Rice C | 6.23 | 25.1 | 16.2 |
| Control A | 1.65 | 5.6 | 5.9 |
| Control B | 1.51 | 5.6 | 5.5 |
| Control C | 5.99 | 22.3 | 13.7 |
| Control D | 5.75 | 5.6 | 2.5 |
| Blank Control | 0.005 | 5.5 | 2.3 |

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of producing an agricultural product for improving immunity, the agriculture product being rice, comprising:
   (1) soaking seeds of the agricultural product in a solution, wherein the solution comprises a composition comprising a magnetic material and a β-glucan;
   (2) before planting the seeds, applying a bottom fertilizer to a paddy field for the agricultural product, wherein the bottom fertilizer comprises a composition comprising an organic fertilizer, a magnetic material, an oyster shell powder, a β-glucan and an organic zinc; and
   (3) at tillering stage, applying a topdressing to the paddy filed, wherein the topdressing comprises a composition comprising a β-glucan and an organic zinc,
   wherein the magnetic material of step (1) and step (2) is a mixture of a ferrite powder and a magnetite powder.

2. The method of claim 1, further comprising:
   at grain filling stage, spraying the β-glucan and the organic zinc to the agricultural product.

3. The method of claim 1, wherein the β-glucan is a yeast β-glucan.

4. The method of claim 1, wherein the organic zinc is zinc gluconate or zinc ferment.

5. The method of claim 1, wherein the solution is an aqueous solution containing 2-5 wt % of the magnetic material by weight and 1-1.5 wt % of the β-glucan, based on the weight of the aqueous solution.

6. The method of claim 1, wherein the seeds are sonicated in the solution for 30-60 minutes.

7. The method of claim 1, wherein the bottom fertilizer includes 5-8 wt % of the magnetic material, 15-25 wt % of the oyster shell powder, 3-5 wt % of the β-glucan and the 2-5 wt % of the organic zinc, based on the weight of the organic fertilizer.

8. The method of claim 7, wherein the organic fertilizer, the magnetic material, the oyster shell powder, the β-glucan and the organic zinc are stirred for at least 20 minutes at 45-60° C. before applying the bottom fertilizer.

9. The method of claim 1, where the topdressing includes 3-5 wt % of the β-glucan and 2-5 wt % the organic zinc, based on the weight of the topdressing.

10. The method of claim 2, wherein the β-glucan and the organic zinc are dissolved in 200-500 times weight of water before spraying to the agricultural product.

* * * * *